United States Patent [19]

Doutre et al.

[11] Patent Number: 5,031,444
[45] Date of Patent: Jul. 16, 1991

[54] METHOD AND APPARATUS FOR THE DETERMINATION OF GAS CONCENTRATION IN MOLTEN METAL AND METAL MATRIX COMPOSITES

[75] Inventors: Don A. Doutre, Kingston; Ghyslain Dube, Jonquiere; Jean-Pierre Martin, Chicoutimi-Nord; Gaston Riverin, Jonquiere, all of Canada

[73] Assignee: Alcan International Limited, Montreal, Canada

[21] Appl. No.: 437,980

[22] Filed: Nov. 16, 1989

Related U.S. Application Data

[63] Continuation-in-part of Ser. No. 199,673, May 27, 1988, Pat. No. 4,907,440.

[30] Foreign Application Priority Data

Nov. 17, 1988 [CA] Canada .................................. 583426

[51] Int. Cl.$^5$ .............................................. G01N 7/10
[52] U.S. Cl. ...................................................... 73/19.07
[58] Field of Search ..................................... 73/19, 23

[56] References Cited

U.S. PATENT DOCUMENTS

| 2,861,450 | 11/1958 | Ransley | 73/19 |
| 4,257,257 | 3/1981 | Dairaku et al. | 73/19 |
| 4,454,748 | 6/1984 | Terai et al. | 73/19 |
| 4,757,707 | 7/1988 | Harvey et al. | 73/19 |

FOREIGN PATENT DOCUMENTS

| 148342 | 7/1986 | Japan | 73/19 |
| 415894 | 7/1974 | U.S.S.R. | 73/19 |
| 913152 | 3/1982 | U.S.S.R. | 73/19 |
| 1004816 | 3/1983 | U.S.S.R. | 73/19 |

Primary Examiner—Hezron E. Williams
Assistant Examiner—Joseph W. Roskos
Attorney, Agent, or Firm—Cooper & Dunham

[57] ABSTRACT

The invention provides a new method for the determination of the concentration of gas dissolved in a molten metal or metal matrix composite employing a new immersion head probe in apparatus employing the method. Such determinations are needed to facilitate removal of the gas, which can cause loss of desirable properties and/or bubbles in the solidified material and subsequent processing difficulties. This determination is particularly difficult with metals containing high concentrations of particulate additions, such as metal matrix composites, since it is necessary to avoid deposition of the particulates and consequent inaccurate readings. The method employs apparatus which circulates an inert carrier gas through the probe in gas exchange contact with the molten metal to entrain dissolved gas until an equilibrium mixture is obtained; the concentration of the dissolved gas in the mixture then is representative of its concentration in the molten metal. The head consists of a monolithic or integral body of a porous gas-permeable material of sufficient porosity, pore size and permeability to permit the necessary gas diffusion in a reasonable period of time. If the test is to be carried out in a stationary body of molten metal, the probe may be vibrated or the metal may be stirred.

23 Claims, 8 Drawing Sheets

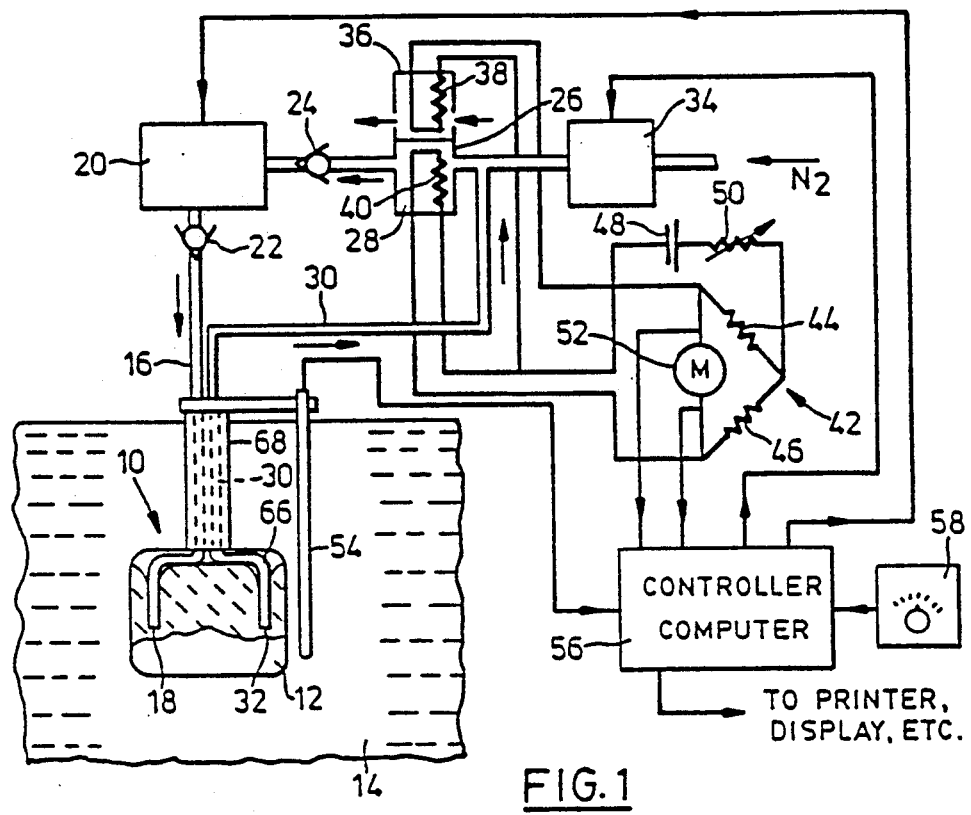
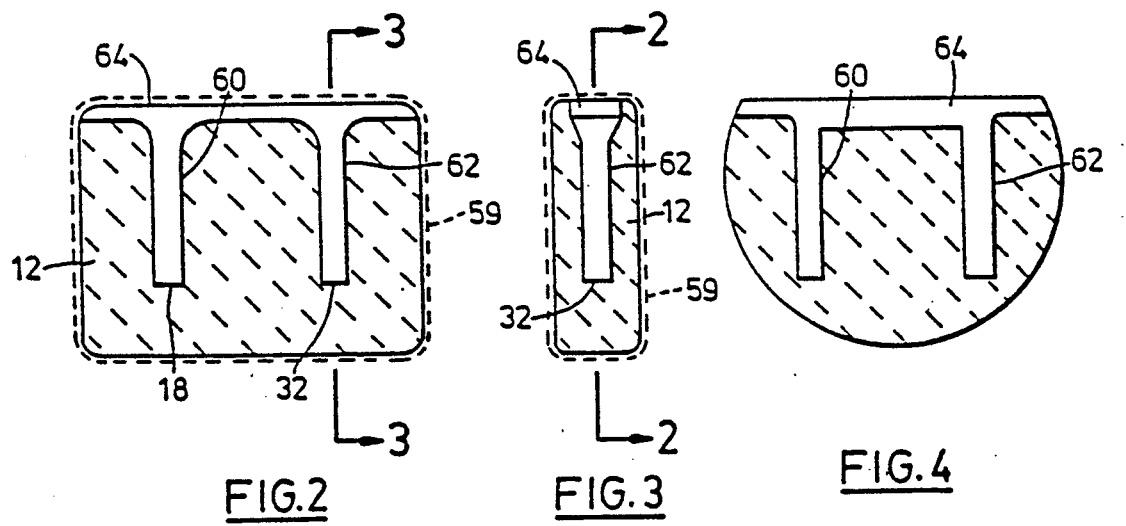
FIG.2  FIG.3  FIG.4

FIG.18

METHOD AND APPARATUS FOR THE DETERMINATION OF GAS CONCENTRATION IN MOLTEN METAL AND METAL MATRIX COMPOSITES

CROSS-REFERENCE TO RELATED APPLICATION

This application is a continuation-in-part of U.S. Ser. No. 199,673, filed May 27, 1988, now U.S. Pat. No. 4,907,440, issued Mar. 13, 1990, of Jean-Pierre Martin, Ghyslain Dube, and Don A. Doutre (three of the applicants herein), for "Probe for Determination of Gas Concentration in Molten Metal," and assigned to the same assignee as the present application.

FIELD OF THE INVENTION

The present invention relates to a method for measuring the concentration of a gas such as hydrogen dissolved in a molten metal or in a metal matrix composite, so as to permit the total content of the gas in the metal to be determined, and to apparatus employing such a method. More particularly, the invention is concerned with a method and apparatus for direct measurement of the content of hydrogen dissolved in liquid metal, more specifically molten aluminum and alloys thereof.

REVIEW OF THE PRIOR ART

Many metals including aluminum and its alloys when in the liquid state react chemically quite readily with the moisture in the atmosphere to form gaseous hydrogen which, owing to its high solubility will dissolve readily in the liquid metal. This is particularly true of aluminum and its alloys and for convenience the following discussion will make reference principally to this metal. Thus, the solubility of hydrogen in aluminum and its alloys is particularly high, about 1 mL STP/100 grams at the melting temperature (about 700° C.), but the solubility in the solid metal is only about one-tenth of this value, and this dissolved hydrogen can generate serious problems during further processing of the solid metal. For example, during solidification there is a strong tendency for the excess gas to be expelled from the metal, leading to the formation of blow holes and gas bubbles which are trapped therein. Such bubbles lead to the formation of cracks in the cast ingots, which can have disastrous consequences during subsequent rolling operations, and can ruin the surface finish of thin foil products. There is therefore an increasing requirement to degas the molten metal prior to the metal casting process. Degassing processes usually comprise the introduction of chlorine gas and/or an inert gas such as nitrogen or argon into the molten body or stream of metal in the form of a dispersion of fine bubbles. Typically dilute mixtures of chlorine in argon are used with one or more lances or rotating impellers to introduce the degassing media into the melt. The efficient operation of the degassing process requires an accurate knowledge of the concentration of the hydrogen gas in the metal, so that its total content can be determined, and numerous techniques exist for such measurement. Most of these techniques require the preparation of a solid sample and access to sophisticated analytical equipment suitable only for use in a laboratory setting and not the relatively arduous conditions of a metal casting shop. Moreover, although these methods are precise they are relatively slow and do not allow the necessary information to be obtained "on-line" during the progress of a casting operation.

Another group of metal products for which accurate determination of gas content, particularly hydrogen content, is important, are metal matrix composites consisting of a base metal, usually aluminum, reinforced by the incorporation therein of substantial quantities of non-metallic particulate materials (e.g. silicon carbide, alumina, titanium diboride, etc.) uniformly distributed throughout the base metal. It is found that the presence of hydrogen is deleterious to the desired properties of the composites, and it is a standard step in the processes for their production to remove the absorbed hydrogen from the molten metal. This may be achieved by vacuum degassing the composite melt while molten. Examples of such processes are given in U.S. Pat. No. 4,759,995, issued July 26, 1988 to Dural Aluminum Composites Corporation, the disclosure of which is incorporated herein by this reference. The introduction and retention of large quantities of non-metallic particulates (up to 40% by volume or 50% by weight) uniformly distributed in the base metal is difficult, requiring continued agitation of the molten mixture, and rapid "on-line" determination of the gas content is therefore even more essential.

There is at present only one method known to the applicants which enables direct measurement within the molten metal and allows on-line analysis in the plant, namely the "Telegas" process, as described in U.S. Pat. No. 2,861,450 of Ransley et al. The "Telegas" apparatus comprises a probe immersion head which is immersed in the molten metal, the head comprising an inverted collector cup or bell of heat resistant impervious ceramic material whose mouth is closed by a ceramic filter to form a chamber within its interior. A first capillary tube extends downward through the head and the filter, while a second such tube extends upward from the interior of the chamber. A fixed quantity of an inert gas, usually nitrogen, is circulated in the apparatus by feeding it down through the first tube and withdrawing it through the second tube, so that it bubbles into the molten metal adjacent the head, the bell collecting the upwardly-moving bubbles, while the ceramic filter prevents the molten metal from entering the enclosure. The nitrogen entrains some of the hydrogen in the adjacent metal and is constantly recirculated for a sufficient length of time, usually about 5 to 10 minutes, until the partial pressure of the hydrogen gas in the nitrogen/hydrogen mixture reaches an equilibrium value. Owing to the high mobility of the dissolved hydrogen in the molten metal, this will accurately represent the hydrogen concentration throughout the body of the melt.

As equilibrium is approached the concentration of the hydrogen in the carrier gas is monitored by measuring the difference in electrical resistance of two like hot-wire detecting elements disposed in respective equal measuring cells, one of which receives the nitrogen/hydrogen mixture and the other of which has an atmosphere whose thermal conductivity is substantially equal to that of the nitrogen, usually air. The difference in resistance is measured by a bridge circuit, the value being calibrated to correspond to the hydrogen gas concentration value, as determined by any of the laboratory-type analytical apparatus mentioned above. This measured value will need to be compensated for melt temperature, and also for the different solubility of hydrogen in the specific metal or alloy with which the apparatus is employed, by any of the methods well known to those skilled in this particular art.

There are several technical problems connected with this type of immersion head. Firstly, the probes are made of high density ceramic materials in order to be resistant to the molten metal and also to be impervious to diffusion of the hydrogen therethrough, so that faulty readings will not be obtained. Such materials have very low resistance to thermal and mechanical shock, and any mishandling leads to damage or even destruction. For example, it is essential in practice to preheat the probe before immersion by positioning it close to the body of molten metal, and to insert it and withdraw it slowly from the metal in order to prevent such thermal shocks. Again, such a probe theoretically should be effective for 20 to 30 analyses before requiring replacement, but it is not unknown for them to become useless after only three immersions in the melt. The usual cause of this is splashing of the liquid metal during the part of the analysis cycle in which the gas mixture is purged from the probe, this metal blocking the porous ceramic element so that it cannot perform its function. Further, because of the design the probes are relatively expensive to produce. Difficulties also arise in obtaining rapid and accurate analyses, owing to the particular shape of the probe. Thus, if the probe is not kept vertical in the molten metal, some of the carrier gas may escape from beneath the cup to the surface, leading to an erroneous reading. Moreover, the gas that bubbles from the first conduit ideally should disperse uniformly in the adjacent body of metal, but instead tends to stay close to the outside wall of the conduit, so that the recirculation time is considerably increased.

Owing to the size of the probe a minimum metal depth of 7.5 cm. (3 ins.) is required in the metal bath for effective operation. This is sometimes difficult in the production of metal matrix composites which may involve measurement in the molten metal flowing in a shallow layer in a transfer through between the furnace and the casting station. Moreover, the "Telegas" probe requires an initial period of substantial length during which the carrier gas bubbles through the body of the metal adjacent the probe; this may cause the melt to become locally inhomogeneous, at least in the neighbourhood of the probe. The shape of the probe with its inverted bell cavity for trapping the hydrogen makes it particularly susceptible to the deposition of particulate material that can obstruct the gas flow and lengthen the time required for the test to be complete, and may even stop the flow completely.

Another form of immersion probe has been disclosed in a paper by R. N. Dokken and J. F. Pelton, of Union Carbide Corporation, entitled "In-Line Hydrogen Analysis in Molten Aluminum" and presented in an international seminar on refining and alloying of liquid aluminum and ferro alloys held in Trondheim, Norway on Aug. 26–28, 1985. The probe is also the subject of U.S. Pat. No. 4,624,128 issued Nov. 25, 1986 to Union Carbide Corporation. This probe was intended to replace the "Telegas" probe and correct deficiencies perceived therein, such as the possibility that the recirculating gas forms an envelope around the tip of the probe to cause a loss of carrier gas and consequent inaccuracy. This probe comprises two long concentric metallic tubes attached to two heavier metallic tubes. The outer tubes are protected from dissolution into the aluminum by having a woven ceramic blanket covering their outer surfaces. The two heavier tubes are the measuring head of the probe, with the spaces within the ceramic fiber weave providing a zone for the transfer of hydrogen from the molten aluminum to argon carrier gas in these spaces. This carrier gas is recirculated through the two long concentric tubes up to the measuring portion of the instrument.

This probe is essentially a steel structure in which the area of the gas/aluminum exchange surface is of the same order as that of the steel/aluminum contact surface. Hot steel at the operative temperature is quite permeable to hydrogen and is subject to oxidation; the resulting oxidized steel can develop an exothermic reaction with the molten aluminum, and the oxide can react with the hydrogen to form water, leading to false readings. Owing to its design, the regions enclosed by the ceramic weave are effectively "dead" zones having little or no direct contact with the circulating carrier gas, and there is moreover the clear possibility of the inflowing gas "short-circuiting" directly from the inlet to the outlet, leading to longer equilibrium times.

DEFINITION OF THE INVENTION

It is therefore a principal object of the present invention to provide a new method for determining the concentration of gas dissolved in a body of molten metal, particularly to a method that provides an "on-line" direct measurement of such gas concentration, and more particularly to a method that permits such measurement of the concentration of hydrogen in aluminum, aluminum alloys and aluminum metal matrices of composite materials.

In accordance with the present invention there is provided a method for determination of the concentration of a gas dissolved in a molten metal, including the steps of:

immersing in the molten metal a probe body consisting of a gas-permeable, liquid-metal-impervious material of sufficient heat resistance to withstand said immersion;

the body having a gas inlet to its interior, and a gas outlet therefrom;

the gas inlet and outlet being spaced from one another so that gas passing from the inlet to the outlet traverses a substantial portion of the probe body interior for entrainment of gas diffusing to the interior of the body from the ambient molten metal;

passing a carrier gas through the probe body interior to entrain gas to be determined that has diffused therein from the molten metal; and measuring the concentration in the carrier gas of the gas to be determined.

Also in accordance with the invention there is provided a method for the determination of gas concentration in a molten metal including the steps of:

immersing in the molten metal an immersion probe comprising:

a probe body consisting of- gas-permeable, liquid-metal-impervious material of sufficient heat resistance to withstand immersion in the molten metal;

the body having a gas inlet to its interior and a gas outlet therefrom;

the gas inlet and outlet being spaced from one another so that gas passing from the inlet to the outlet traverses a substantial portion of the probe body interior for entrainment of gas diffusing to the interior of the body from the ambient molten metal;

and recirculating a carrier gas in a closed circuit between the probe and a gas concentration determining means adapted to determine the proportion of the gas present in a mixture thereof with the carrier gas.

Preferably, the gas to be detected is hydrogen and the metal is selected from aluminum, aluminum alloys and aluminum matrix composites.

DESCRIPTION OF THE DRAWINGS

Particular preferred embodiments of the invention will now be described, by way of example, with reference to the accompanying diagrammatic drawings, wherein:

FIG. 1 is a schematic diagram of an apparatus including a probe device for measuring the gas content of a molten metal;

FIG. 2 is a cross-section to a larger scale of the body of the probe device of FIG. 1, taken on the line 2—2 of FIG. 3;

FIG. 3 is another cross-section view of the probe device body taken on the line 3—3 of FIG. 2;

FIG. 4 is a cross-section similar to FIG. 2 of another form of immersion probe body of the invention;

FIGS. 16 through 18 are graphs of test results for different alloys employing the probe of the invention.

DESCRIPTION OF THE PREFERRED EMBODIMENTS

Figure 5:
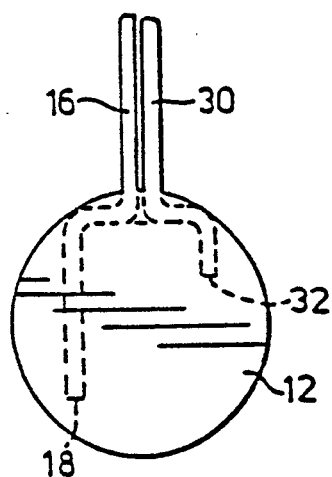
FIGS. 5 through 12 are similar elevational views of different configurations of probe bodies of the invention.

Referring now to FIG. 1 there is shown therein a probe element 10 of the invention, consisting of a monolithic body 12 of gas-permeable, liquid-metal-impervious material, immersed in a body 14 of molten metal, specifically of molten aluminum or an alloy thereof, or a composite thereof. The body 14 may be stationary, as would be obtained in a ladle or a laboratory sample, or it may be a stream of metal, as would be obtained in a transfer trough leading from a casting furnace. The specific structure of the probe element will be described in detail below. A fine bore tube 16 extends from a gas inlet 18 in the body of the probe element to a recirculation pump 20 via a non-return valve 22, and thence via another non-return valve 24 to the gas outlet of the sensing cell 26 of a katharometer 28. Another fine bore tube 30 extends from a gas outlet 32 from the body 12 to the gas inlet to the katharometer sensing cell 26, so as to complete a closed circuit including the probe element, the pump and the cell. The tube 30 includes a T-junction by which the gas circuit is connected to a controllable flushing valve 34 which when opened admits a flushing gas, usually nitrogen, into the circuit from a suitable source, usually a cylinder of the compressed gas (not shown).

In the embodiment of FIG. 1, the comparison cell 36 of the katharometer is open to atmosphere, since ambient air is a suitable comparison medium when the carrier gas is nitrogen. However, if some other carrier gas is used, such as argon, it would then be necessary either to seal the comparison cell containing said gas, or to flow the gas continuously through the cell. Each cell contains a respective fine resistance wire 38 and 40 connected as the respective adjacent arms of a bridge circuit 42. The other bridge arms are constituted in well known manner by resistors 44 and 46, the bridge is supplied with operating current from battery 48 via adjusting resistor 50, and a bridge meter 52 or other measuring device being connected in known manner between the two opposite junctions. A thermocouple 54 is mechanically connected to the probe element 10 so that it is immersed therewith into the molten metal 14 and provides the necessary measurement of the metal temperature.

The thermocouple 54, the pump 20, the flushing valve 34, and the bridge measuring device 52 are all connected to a computer controller 56 which is arranged to automatically control the apparatus through each concentration determining cycle of operations, and to feed the results of the cycle to one or more display and/or recording devices which will be apparent to those skilled in the art.

A typical measurement cycle will begin with the flushing valve 34 being opened by the controller 56, so that dry nitrogen under pressure circulates through the entire circuit, entering at both the probe gas inlet 18 and the outlet 32 and exiting through the porous body of the probe element; this circulation is maintained long enough to ensure that only nitrogen remains in the circuit. On start-up it is also desirable to maintain the flushing for a sufficiently long period to ensure that all moisture has been eliminated. The flushing operation is maintained until the probe has been lowered into the melt when the valve 34 is closed and the pressure of the nitrogen in the circuit will quickly reach a steady value. In practice the flushing is carried out at a gas pressure of about 20 to 50 KPa (3 to 7 p.s.i.), which reduces to a range of about 2 to 8 KPa (0.25 to 1 p.s.i.) during the test procedure. The operation of the pump motor causes the volume of carrier gas in the circuit to be constantly recirculated therein, passing in the body 12 from the inlet 18 to the outlet 32.

Owing to the very high mobility of hydrogen in liquid aluminum at the usual temperatures involved (about 700° C.), it will rapidly and easily enter the porous probe body in attempting to establish concentration equilibrium and become entrained in the carrier gas, the circulation of this gas being maintained for a period of time known to be sufficient to establish equilibrium, usually of the order of 1 to 10 minutes. At the end of this period the controller is operative to take a measurement of the difference in resistivity of the resistance wires 38 and 40 in the katharometer. The nitrogen/hydrogen mixture causes increased cooling of the wire 40 because of the presence of the hydrogen, this increase being a measure of the partial pressure or concentration of the hydrogen in the nitrogen/hydrogen mixture, and thus of the concentration of the dissolved hydrogen in the metal body. The controller will usually be arranged to compute the concentration value directly, as will be apparent to those skilled in the art, including the application of a correction factor from an operator-adjusted circuit 58 to account for the different solubility of hydrogen in different metals and alloys. Upon conclusion of the measurement portion of the cycle the circuit is flushed by a short burst of argon gas to purge hydrogen from the system, so that it is ready for a new cycle. The probe may be removed from the metal or left in place at the choice of the operator.

The improved operation of the probes of the present invention is best described by comparison with the "Telegas" probe which consists of a dense gas-impervious ceramic body from which the nitrogen carrier gas is bubbled into the metal body in direct contact with the metal and the hydrogen dissolved therein. It has been considered necessary for such direct contact to take place to obtain effective entrainment of the hydrogen in the carrier gas. Some of the difficulties obtained in practice with this apparatus have been described above, and its application to the measurement of hydrogen content in metal matrices of composite materials is even more difficult. The large quantities of particulates in such composites result in physical properties and behaviour entirely different from that of the metal and its usual alloys, primarily differences in viscosity and density, with the result that meaningful and reproducible readings become more difficult to obtain. In addition to the deposition and depth problems discussed above, a preheating period of at least 10 minutes is recommended for the "Telegas" probe before it is inserted into the molten metal, to avoid excessive thermal shock to the high density ceramic from which it is mainly fabricated. Owing to the need to keep the particulate component in suspension, and the typically small size of production batches currently in use, the casting time for composites is relatively short and this relatively long preheat period makes it unusable for the purpose.

By contrast a probe element 10 of the invention, by elimination of this bubbling and its replacement with direct diffusion and mixing of the gases within the interstices of the probe body, can consist of a single monolithic or unitary block of material of suitably chosen porosity, pore size and permeability provided with a gas inlet and a gas outlet spaced sufficiently apart that the circulating carrier gas must traverse a substantial portion of the interior of the probe body. The small probe body almost immediately reaches the temperature of the ambient metal, and the hydrogen therefore readily diffuses in the pores of the block, so that it will quickly mix with the carrier gas and attain the necessary equilibrium of concentration.

The elimination of the bubbling period with the method and probe of the invention means that when used with metal matrix composites the particulates in the metal matrix are not disturbed and do nor separate and rise to the surface while the hydrogen is being measured. Many of these particulates have higher densities than liquid aluminum and prevention of such separation is one of the principal difficult problems in this technology. There is therefore no change in the mixture, which remains homogeneous and the quality of the product is preserved. Since the porous, cavity-free probe is not wetted by the liquid metal the problems of agglomeration are prevented, and obstruction by the particles is unlikely to arise. Because of its small size the probe can operate successfully in very shallow vessels or transfer troughs, with a depth as little as 2.5 c.m. (1 in.).

The porosity of a body is usually expressed as a percentage and is simply the proportion of the total volume of the body that is occupied by the voids within the body, a highly porous body having a high percentage of voids. A high porosity has the advantage that the material is usually more resistant to thermal shock, so that the probe can be plunged directly into the metal without preheating, and removed without having to cool it slowly, making it particularly suitable for metal matrix composite production processes which typically employ very short casting times of about 10 to 20 minutes.

There is moreover greater opportunity for diffusion of the hydrogen into the body, circulation of the nitrogen in the body, and mixing of the two gases together. However, a high porosity body inevitably has many large pores and is usually structurally weaker, to the extent that it may be difficult to anchor the tubes 16 and 30 in the body, and the probe may become too fragile for satisfactory handling under industrial testing conditions. Again, because of the large pores of a highly porous body difficulty may be encountered in the liquid metal seeping into the body. The range of porosity for the probe bodies of the invention is from a minimum of about 5% to a maximum of about 80%, but preferably is in the range of about 20% to about 60%, and more preferably is in the range from about 35% to about 40%.

A second important consideration in the choice of suitable materials for the probe body is the pore size, and this can vary over a wide range, namely from about 0.5 micrometers to 2,000 micrometers, since the size of the hydrogen molecules in the metal is of the order of $2 \times 10^{-4}$ micrometers (2 Angstroms), and both gases can diffuse easily even in the smallest size pores. The lower limit is determined more by the impaired resistance of fine-pored materials to thermal shock, while the upper limit is dictated by mechanical assembly problems, as described above and the increased possibility of the molten metal entering the larger pores. For example, with aluminum under normal operating conditions penetration of the metal into the pores will start to become excessive above 1,000 micrometers. The preferred pore size is therefore in the range 10 micrometers to 1,000 micrometers, and more preferably is in the range 100 micrometers to 250 micrometers.

The third important consideration in the material choice is its permeability. A body of porosity and pore size within the preferred ranges may still be unsatisfactory if the cells or voids are completely "closed" off from one another, or are so poorly interconnected that the gases cannot diffuse and mix together within a reasonable period of time.

As previously described, the porosity of the probe body must be due predominantly to interconnected pores or voids so that it is sufficiently permeable to the gases. Permeability may be generally defined as the rate at which a gas or liquid will pass through a material under a specified difference of pressure. Permeability of any given material can be measured by determining the quantity of a fluid (in this case air) that will flow through a thin piece of the material of specified dimensions under a specified low pressure differential.

For flows occurring under low pressure differentials, D'Arcy's Law states:

$$P_e = \frac{QL}{A} \left[ \frac{u}{P} \right] \tag{1}$$

where
 $Q$ = Air flow (m$^3$/s)
 $P_e$ = Specific permeability (m$^2$)
 $L$ = Sample thickness (m)
 $A$ = Sample cross-sectional area (m$^2$)
 $u$ = Air viscosity at the temperature of measurement ($1.84 \times 10^{-5}$ Kg/m-s at 20° C.)
 $P$ = Pressure (Pa)

The permeability is usually expressed in Darcy units, where:

$$1 \text{ Darcy} = 1 \times 10^{-12} \text{ m}^2$$

Therefore equation (1) can be written:

$$P_D = 10^{12} \frac{QL}{A} \left[ \frac{u}{P} \right] \qquad (2)$$

where $P_D$ is the specific permeability expressed in Darcies.

For air at 20° C. and using a pressure differential of 2 in. H$_2$O (500 Pa):

$$P_D = 3.68 \times 10^4 \frac{QL}{A} \qquad (3)$$

With the probes of the invention it is preferred that the permeability be in the range about 2 to about 2,000 Darcies, more specifically in the range about 10 to about 100 Darcies.

The pore size of the material must be such that both of the carrier gas and the hydrogen will diffuse readily therethrough and become mixed with one another, while it must be impossible for the metal to enter more than the surface layer of the probe body. Thus, it is acceptable to find after the conclusion of a measurement cycle that a thin skin of solidified metal has mechanically adhered to the exterior surface of the probe, since this can readily be stripped away before the next cycle without damage to the probe. Theoretically, it would seem to be advantageous for the exterior surface of the probe body to be metal-wettable, so as to obtain a high-diffusion interface between the metal and the probe, but in practice it is found that reproducible results can be obtained with a monolithic body of non-wettable material, particularly if the probe and/or the metal are stirred as described below. The presence of the above-described thin skin of aluminum on the probe surface indicates that the surface has become wetted and once this has taken place the surface will remain wetted. Wetting can be facilitated by precoating the body with a thin layer of a suitable metal such as aluminum, silver, nickel or platinum, as indicated diagrammatically in FIGS. 2 and 3 at 59 by the broken outline. The metal layer can be applied by any of the well-known processes for such deposition such as dipping, spraying, electrolytic, electroless, etc., the layer being preferably of about 10 micrometers (0.0004 in) to 1000 micrometers (0.04 in) in thickness.

It is found particularly advantageous to employ for the coating 59 a material that has a catalytic action toward the hydrogen, promoting association from its monatomic state in the molten aluminum to the molecular diatomic state in the probe body for its entrainment in the carrier gas. A particularly suitable metal for this purpose is platinum, which can readily be deposited in the desired very thin layers from commercially available electroless platinising solutions. Because of its metallic nature platinum will in addition facilitate wetting as described above. As an example of a suitable process the body 12 is immersed in the platinising solution for a brief period which may be from about 5 seconds to about 5 minutes (the specific time depending upon the solution concentration and the coating thickness desired), the solution normally consisting of about 3% concentration of platinum chloride (PtCl$_4$) or hydro-platinochloride (H$_2$PtCl$_4$) in hydrochloric acid, optionally including lead acerate as a buffer. The body is then baked at a temperature above 500° C., usually about 800° C., to ensure that no residual hydrochloric acid remains. The coating obtained is estimated to be of thickness of about 1 micrometer (0.00004 in.) to 100 micrometers (0.004 in.) and thicknesses of about 0.1 micrometer (0.000004 in.) to 1000 micrometers (0.04 in.) are considered to be suitable. It is found that in use the catalytic coating does eventually dissolve away and if the probe body still has sufficient useful life it can easily be re-coated. Other materials that will function in this manner are, for example, palladium, rhodium and nickel.

The shape of the probe is not at all critical, but it is advantageous that in at least one dimension it be as small as is practical, so as to provide a corresponding minimum path length for the hydrogen to diffuse into the block interior. Preference is also given to shapes that maximize the active metal/probe surface area for a given probe volume. These considerations give preference to the shape of a thin wafer, as illustrated by FIGS. 2 and 3, that is rectangular in all elevations. It will be noted that wherever possible edges of the body are rounded so as to avoid as much as possible sharp corners that are particularly susceptible to mechanical shock. The thickness of the probe to provide the desired minimum path length should be between about 0.5 cm and 1.5 cm, the minimum value being determined also by the mechanical strength of the material and thus of the resultant wafer. Advantageously the volume of the probe is between 1 cc and 10 cc, preferably from 2 cc to about 5 cc.

Referring again to FIGS. 1 to 3, it will be seen that in this particular embodiment the probe body 12 is provided with two parallel bores 60 and 62 which respectively receive the ends of the two tubes 16 and 30; the bores extend into a groove 64 in which the tubes are bent to lie and into which they are fastened by a layer of a suitable heat resistant cement 66 (FIG. 1). This structure brings the two tubes closer together, as seen in FIG. 1, to facilitate their enclosure in a sheath 68 of a heat resistant material, such as a material woven from an alumina fibre, and at the same time provides added resistance to torques that are applied to the body during its handling and its immersion, etc. in the body of liquid metal.

In constructing an apparatus of this type it is desirable to keep the volume of carrier gas that is required as small as possible, so as to decrease the time required for equilibrium to be reached, and this consideration dictates the use of narrow bore tubes 16 and 30, a miniature recirculating pump 20 and a probe 10 of small volume. It will be understood that the volume of gas to fill the probe will be at most the volume of the voids therein. A practical volume for a complete system is between 1 cc and 5 cc, while a practical gas flow rate to obtain a reasonably short response time is from about 50 cc to about 200 cc per minute. However, as the volume of the probe is reduced there is a correspondingly reduced access of the metal and the hydrogen in the melt to the carrier gas and a compromise is therefore necessary. A very successful probe of the invention consists of a porous circular-segment alumina disc as shown in FIG. 4 of porosity about 35% to 40%, average pore size about 120 micrometers and permeability about 25 Darcies. The body has a thickness 0.64 cm (0.25 in.) and diameter 2.5 cm (1.00 in.) to have a volume of about 3 cc (0.3 inch cubed).

It will be seen that a simple monolithic block of such shape is easy to manufacture by well known procedures. Because of its compact configuration, such a body inherently has high resistance to mechanical shock. Moreover, since it is operative totally immersed in the liquid metal with the exchange of hydrogen between probe and metal taking place through the probe body surface, and the hydrogen entrainment into the carrier gas taking place entirely within the interior of the probe body, then its atitude and positioning in the metal body is completely non-critical avoiding this possibility of error. It will also be noted that because of this internalization of the mixing or entrainment mechanism the probe is able to operate successfully in a fast-moving stream of metal, such as in a transfer trough, which is not the case with a probe relying on external bubbling for entrainment, when the bubbles may be swept away before they can return into the probe. The material must be refractory in nature, namely able to withstand the temperature of immersion without softening to an unacceptable degree, and as non-reactive as possible with the metal, since such reactivity will eventually require the probe body to be replaced. A very satisfactory probe material for use in aluminum is fused granular alumina, the grains being held together by a porcelanic bond; such materials of a wide range of porosities are commercially available.

It will be seen that the probes of the invention can easily be made entirely of non-metals, avoiding problems of corrosion and diffusion of the hydrogen, which at the temperatures involved will diffuse through most commercially useful metals. By suitable choice of the porous material used for the body it is possible to obtain a large gas exchange surface in a compact monolithic or unitary integral body, with a maximum of the body volume occupied by the pores and minimum of "dead volume" occupied by the solid material.

Figure 6:
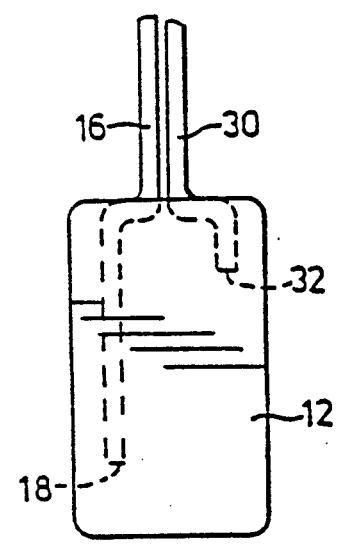
Figure 7:
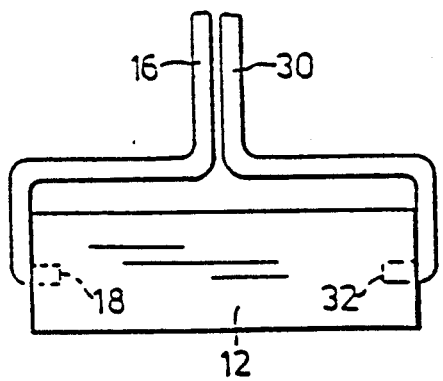
Figure 8:
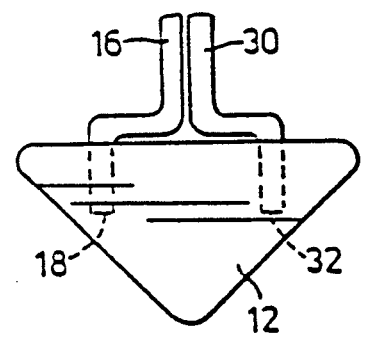
Figure 9:
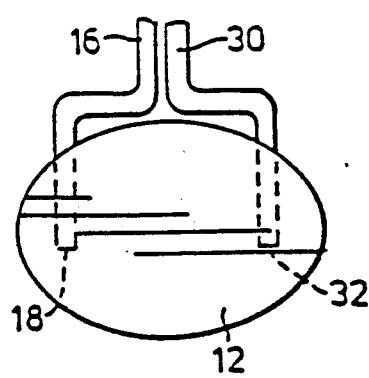
Figure 10:
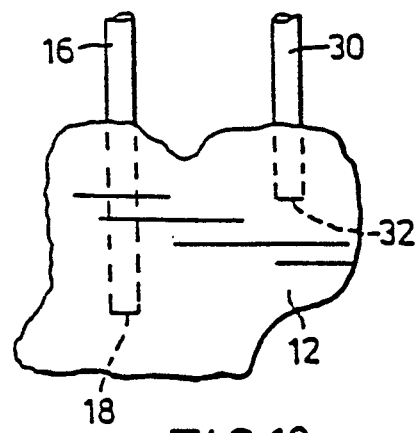
Figure 11:
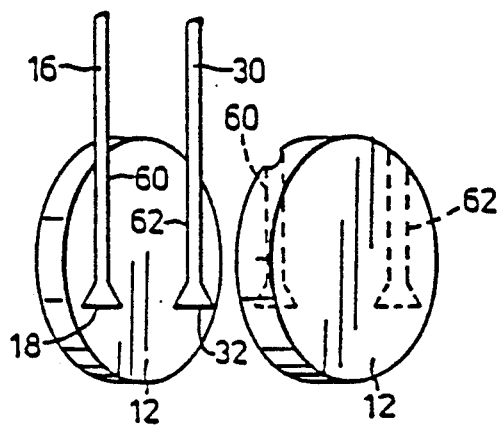
Figure 12:
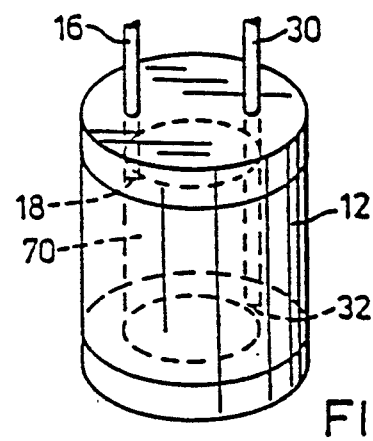

The probes of the invention can take a number of different forms, and some examples are shown in FIGS. 4 through 12. As previously described, the embodiment of FIG. 4 is formed as the major segment of a flat circular disc, while that of FIG. 5 is a complete circular disc, the tubes 16 and 30 extending different distances into the body 12 to increase the length of the flow path between the inlet 18 and outlet 32. FIG. 6 shows a rectangular body that is somewhat longer than it is wide, with the tubes 16 and 30 extending different distances into the body, as with the structure of FIG. 5, while FIG. 7 shows a probe with a cylindrical body, the tubes 16 and 30 entering at opposite ends. FIG. 8 illustrates a triangular-shaped probe body and FIG. 9 an elliptical-shaped body, while FIG. 10 shows that a quite irregular-shaped body of a suitable material can be provided with a gas inlet and outlet and function successfully. FIG. 11 illustrates the fact that the body is not necessarily monolithic, i.e. formed from a single block of material, but instead can be an integral body that is assembled from more than one piece joined together by a suitable cement (not shown), care being taken to ensure that the cement layer does not constitute a barrier to free diffusion of the gases through the body from the inlet to the outlet. The bores 60 and 62 are in this embodiment constituted by mating semi-circular cross-section grooves. FIG. 12 illustrates another integral structure containing a large open void 70 into which the tubes 16 and 30 discharge, the hydrogen diffusing into this volume through the wall of the probe body; such a structure does permit a somewhat less porous material to be used for the body, since hydrogen diffuses more easily than nitrogen and only the hydrogen needs to diffuse through the body. The size of the void 70 should not be such that it increases substantially the response time of the probe.

The probes of the invention have been described in connection with the determination of hydrogen concentration in aluminum and its alloys, but can of course be used for the determination of this and other gases in other metals, such as magnesium, copper, zinc, steel and their alloys.

There is a wide range of manufactured and naturally-occurring materials that can be used to form an immersion probe of the invention, provided of course that upon test they are able to meet the requirement of the combination of mechanical strength, porosity, pore size and permeability. Examples of synthetic materials are:

(a) Porous ceramics that are sufficiently refractory in nature to be used with the metal under test, including the carbides, nitrides and oxides of aluminum, magnesium, silicon, zirconium, tungsten and titanium;

(b) Ceramic foams and fibres;

(c) Grinding materials and synthetic minerals, particularly the silicates and spinels;

(d) Composites of fibres in metal matrices;

sintered metal powders of sufficiently high melting point, e.g. steel, titanium and tungsten; since such materials are metal-wettable they should be provided with a gas-permeable coating of a metal non-wettable material;

(e) Porous graphite and other carbon based materials, including fibres of such materials in mat form or embedded in a suitable matrix; and (f) Filtered porous glasses of sufficiently high melting point, such as pyrex and aluminosilicates; porcelains.

Examples of naturally-occurring materials are mullites, sandstones, and pumices. The materials can be prepared to have the necessary properties and shape by any of the well known techniques, such as sintering, pressing, binding, gas forming, moulding, drilling, grinding, etc.

When use of the probes of the invention involves their immersion in a moving stream of metal, the movement of the metal past the probe (typically of the order of 5 cm/sec) ensures adequate contact between the probe surface and the metal to obtain a reasonably short response time to nitrogen/hydrogen equilibrium. However, as with any probe this period is increased if the bath is static. Owing to the inherent structure of the probes it is possible to shorten the test time in a static bath by creating an artificial relative movement between the probe and the metal. This is not possible with prior art probes using external bubbling because of the danger of loss of the circulating carrier gas if it does not remain sufficiently close to the probe to be recaptured thereby. Thus, it is found that the response time with the probes of the invention can be reduced to values of about 2 to 5 minutes by use of the embodiments illustrated by FIGS. 13 to 15.

Figure 13:
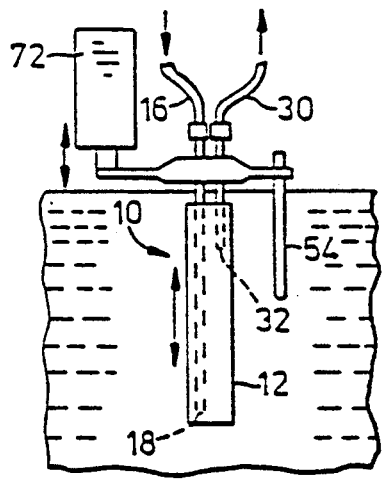
FIGS. 13 through 15 illustrate different arrangements of the probe device to increase contact between the probe body surface and the liquid metal.

With the apparatus of FIG. 13 the probe element 10 is mounted on a vibrator 72, the movements of the probe produced by the vibrator 72 facilitating the diffusion of the hydrogen across the probe/metal interface. The vibrator can be of mechanical or magnetostrictive type and vibrates the probe in any mode that it produces.

Figure 14:
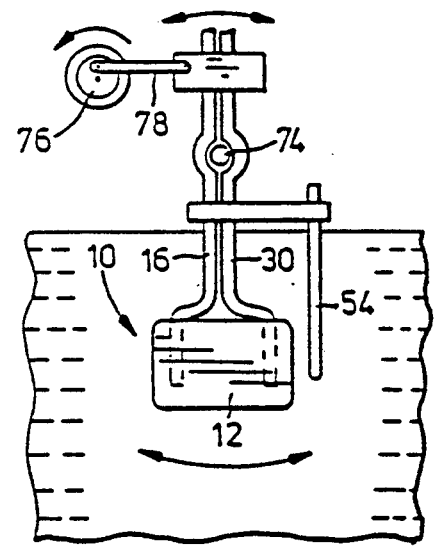

With the apparatus of FIG. 14 the probe is mounted to rock about a pivot 74 under the action of a motor-driven eccentric 76 connected to the probe support by a shaft 78. With both systems the range of movement of the probe is preferably in the range 0.5 to 5 Hertz, more preferably in the range 1 to 2 Hertz, and with a mechanical excursion in the range 10 to 100 mm.

Figure 15:
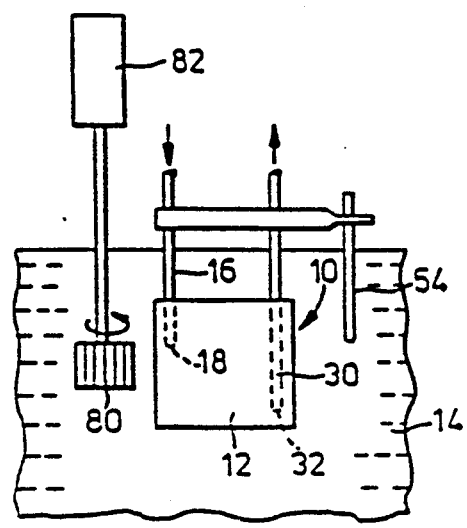

With the apparatus of FIG. 15 the probe is stationary during the test, and instead the molten metal is circulated around the probe by means of a small impeller 80 driven by a motor 82, this circulation again facilitating diffusion at the probe/metal interface. An impeller of about 8 cm diameter rotating at speeds in the range of 100 to 400 r.p.m. is found to be completely effective.

To determine the effectiveness of the probes of the invention 28 different probes were employed in comparison tests that were confirmed using existing laboratory instruments. Each probe was tested under static conditions for three repeat measurements being taken out of the metal bath, comprising a small laboratory furnace at temperatures from 700° C. to 750° C., between each test. The values obtained ranged from 0.05 to 0.45 ml/100 g, with most values in the range 0.15 to 0.25 ml/100 g for four different alloy types, namely:
(a) commercially pure aluminum (99.5%);
(b) aluminum/magnesium alloys-including up to 5% by weight Mg;
(c) aluminum/zinc/magnesium alloys including up to 5% by weight Zn and up to 2% Mg
(d) aluminum/lithium alloys including up to 3% by weight Li The overall probe to probe reproducibility (84 values) was 0.017 ml/100 g, while the average repeatability of the same probe was 0.012 ml/100 g. The usual response time under these static conditions was 8 to 10 minutes. The precision of these values may be compared with the reproducibility values of 0.03 to 0.05 ml/100 g obtained with a nitrogen carrier fusion laboratory-type analyser.

Figure 16:
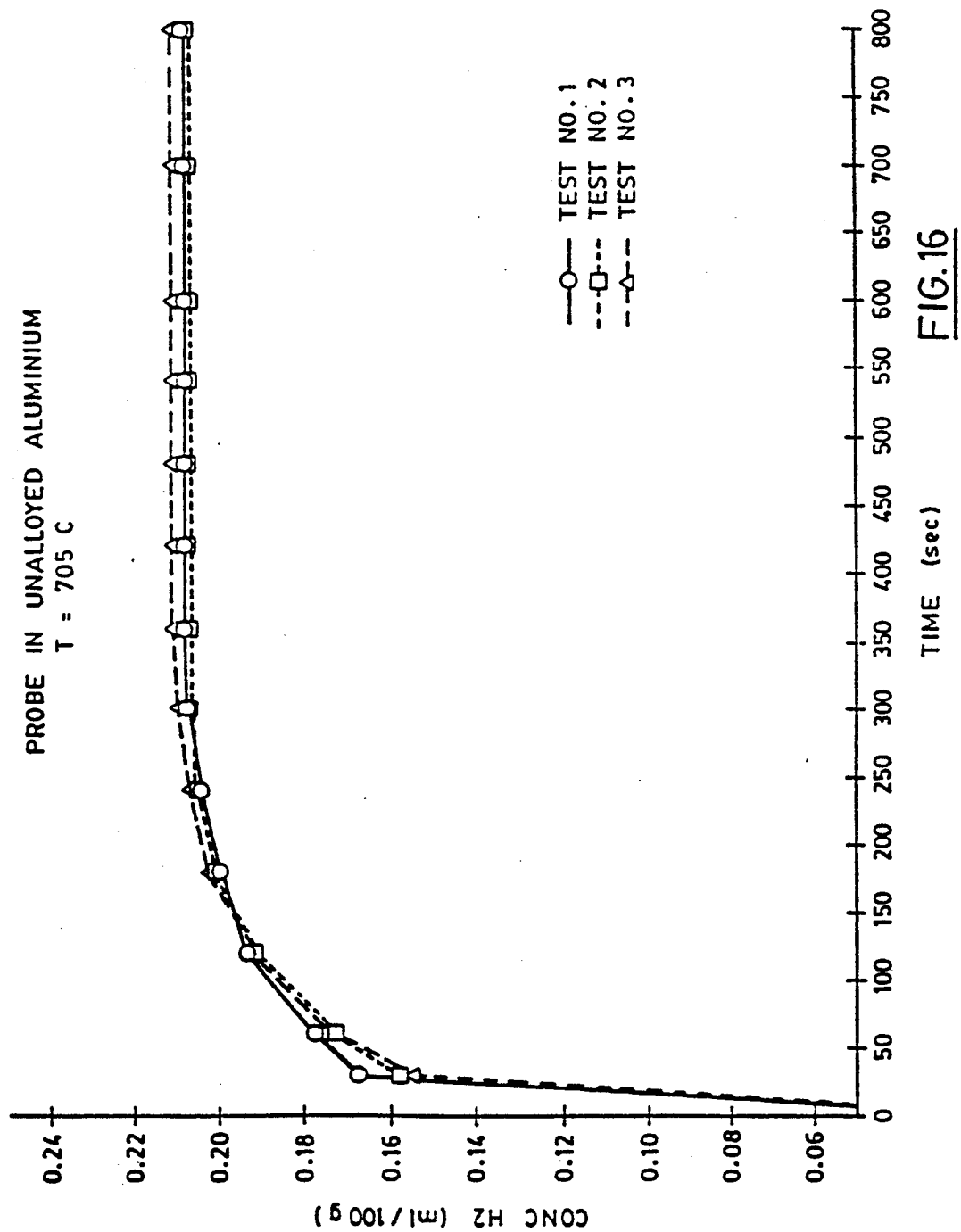
Figure 17:
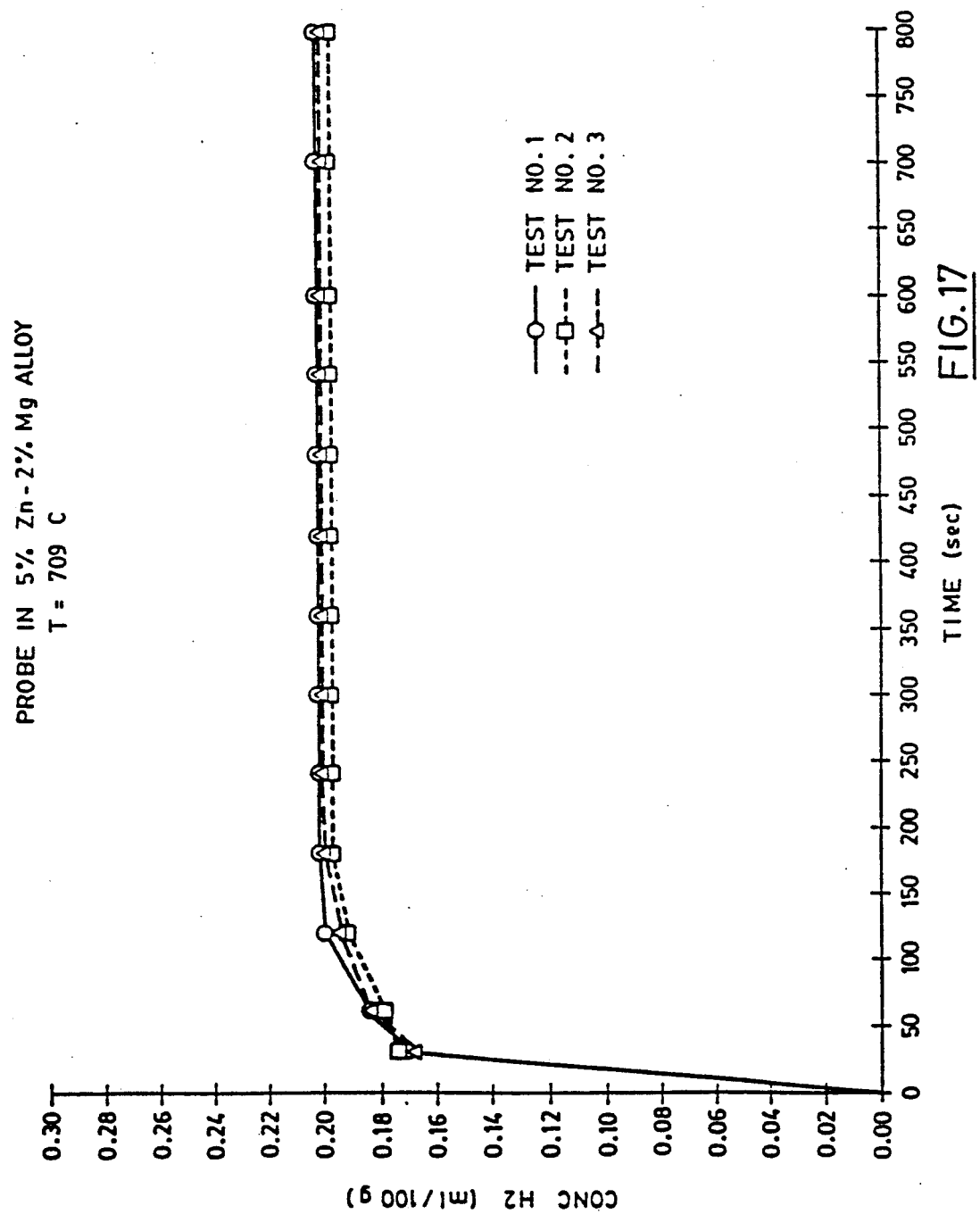
Figure 18:
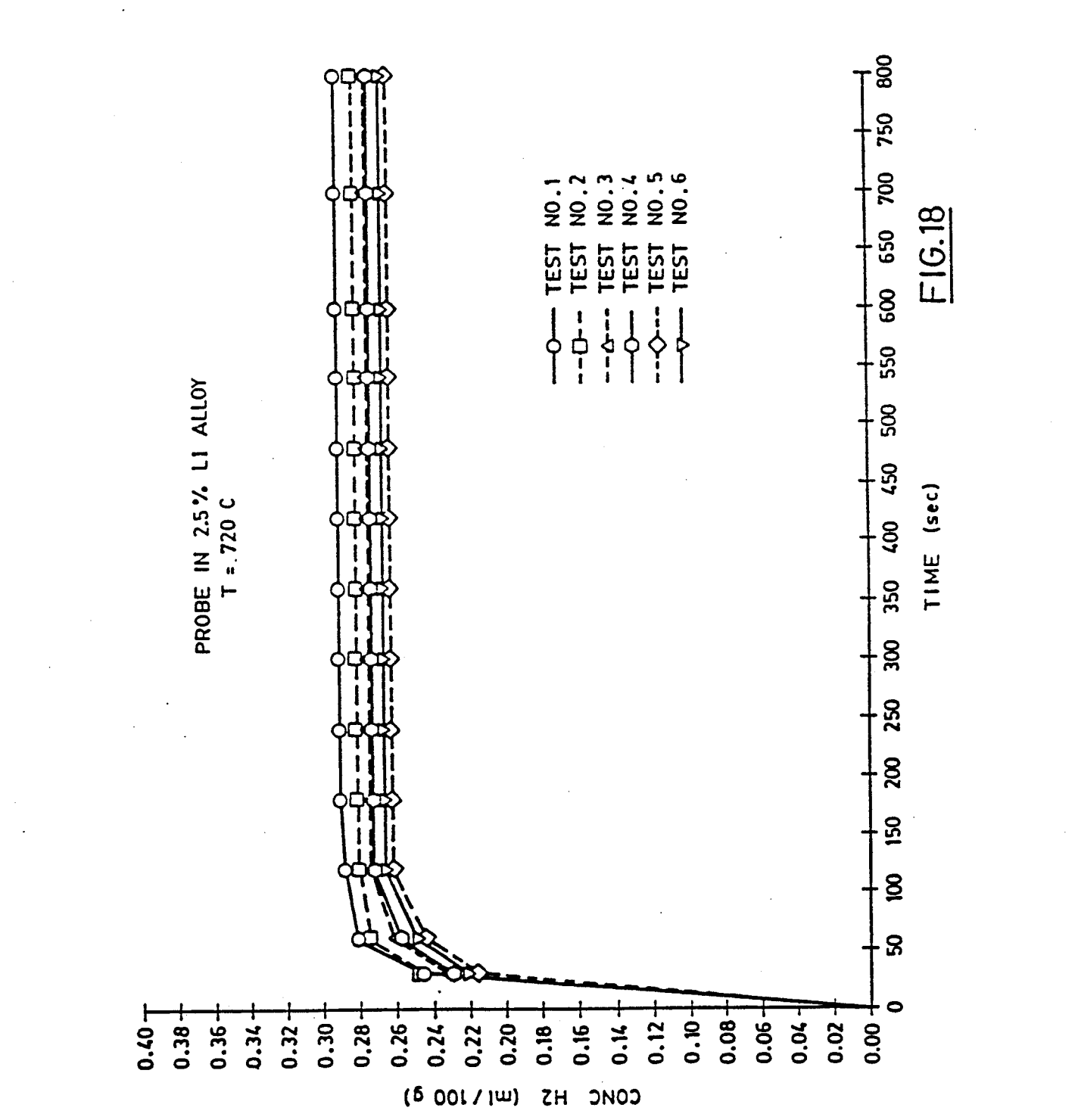

FIGS. 16 through 18 are test results obtained with the following metals:
FIG. 16: Unalloyed aluminum at 705° C.
FIG. 17: Al/Zn/MG alloy with 5% Zn and 2% Mg at 709° C.
FIG. 18: Al/Li alloy with 2.5% Li at 720° C.

The reproducibility of all of the results will be noted. Adequate equilibrium for testing was reached with the unalloyed aluminum in 5 minutes with an acceptable value at 4 minutes. The results obtained with the Al/Zn/Mg alloy were even faster with acceptable equilibrium at a little over 2 minutes and complete equilibrium at 3 minutes. Complete equilibrium was reached with the Al/Li alloy in 2 minutes, with the reproducibility differing the most, namely over the range 0.26 to 0.29 ml per 100 g. Lithium alloys are difficult to test with conventional laboratory methods. In most laboratory test procedures as a solid sample of the alloy is heated to a temperature sufficient to release the hydrogen the lithium also is released and good reproducibility is correspondingly difficult to obtain. Its alloys therefore require special handling.

A series of experimental tests was carried out using the method and probe of the invention for the determination of hydrogen concentration in aluminum composites, consisting of the aluminum alloys A356, 1100, 2014 and 6061 having incorporated therein from about 5% to 40% by volume of two different reinforcing particulates, namely silicon carbide (SiC) and aluminum oxide ($Al_2O_3$). The capacity of the production unit was 100 kg. (220 lbs.) and the casting time employed was about 15 minutes with no preheating of the probe above the metal, the depth of metal in the casting box being 5 cms. (2 ins.). The "Telegas" probe could not be used because of the shallow casting box, and because the short casting time did not permit the necessary preheating of the probe.

Figure 19:
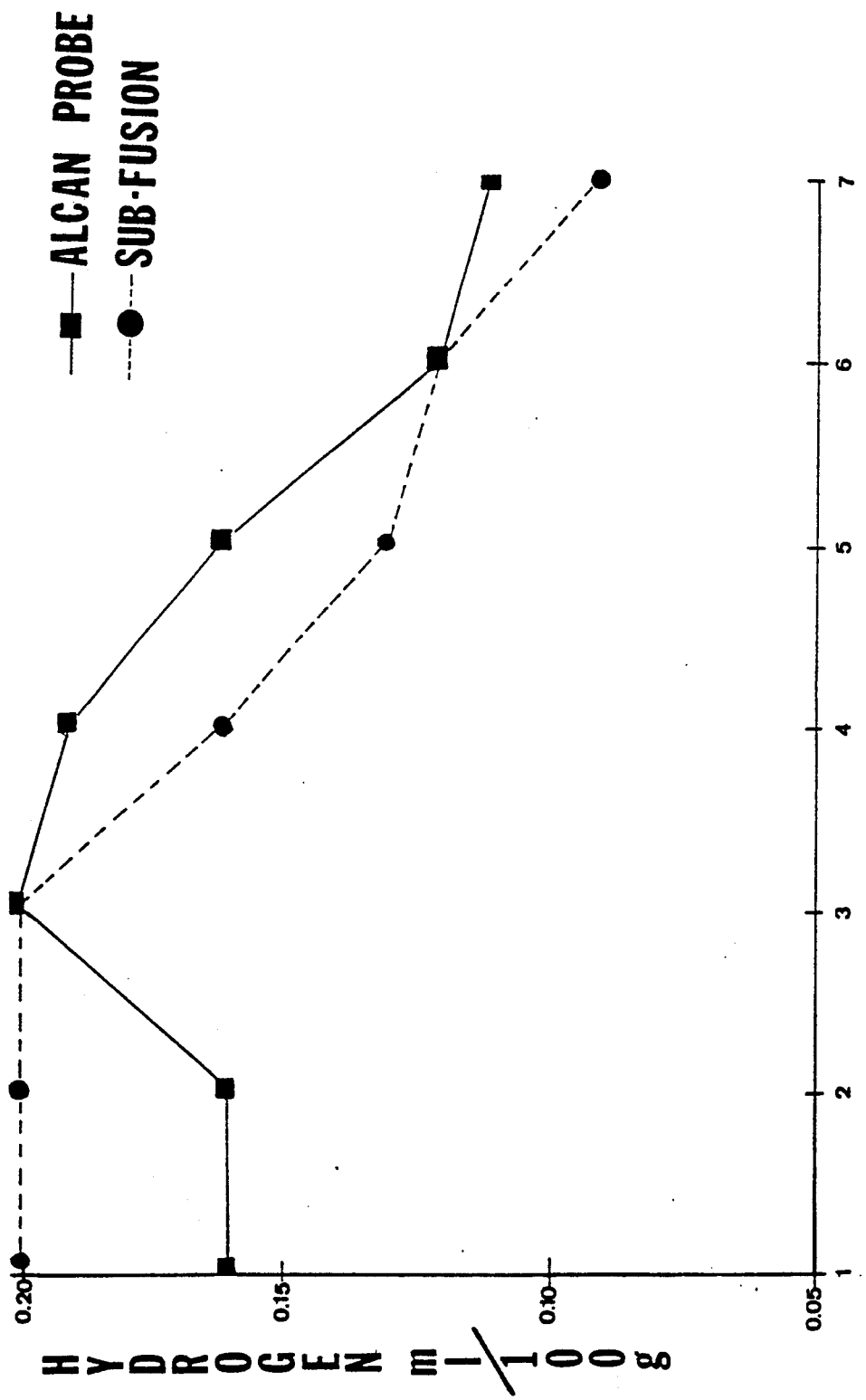
FIGS. 19 and 20 are graphs of test results employing the method and probe of the invention with various aluminum matrix composites.

Other tests were carried out on metal composite materials in a 50 kg. (110 lbs.) laboratory unit crucible, employing the two alloys A356 and 6061, and again incorporating the silicon carbide and aluminum particulates, but in the smaller amounts of about 10% to 15% by volume. FIG. 19 shows by a solid line the results of hydrogen measurements taken with alloys 1100 and 6061, these results being reproducible. During these measurements Ransley samples were taken and the absolute hydrogen content of the solidified metal measured by subfusion as described by C. E. Ransley and D. E. J. Talbot in J. Inst. Met. No. 84, 1955–56, pages 445–452. The results are shown by the broken line in FIG. 19 and correlate well with an average error of 0.02 mL./100 g., using the subfusion method as the reference value by convention.

Figure 20:
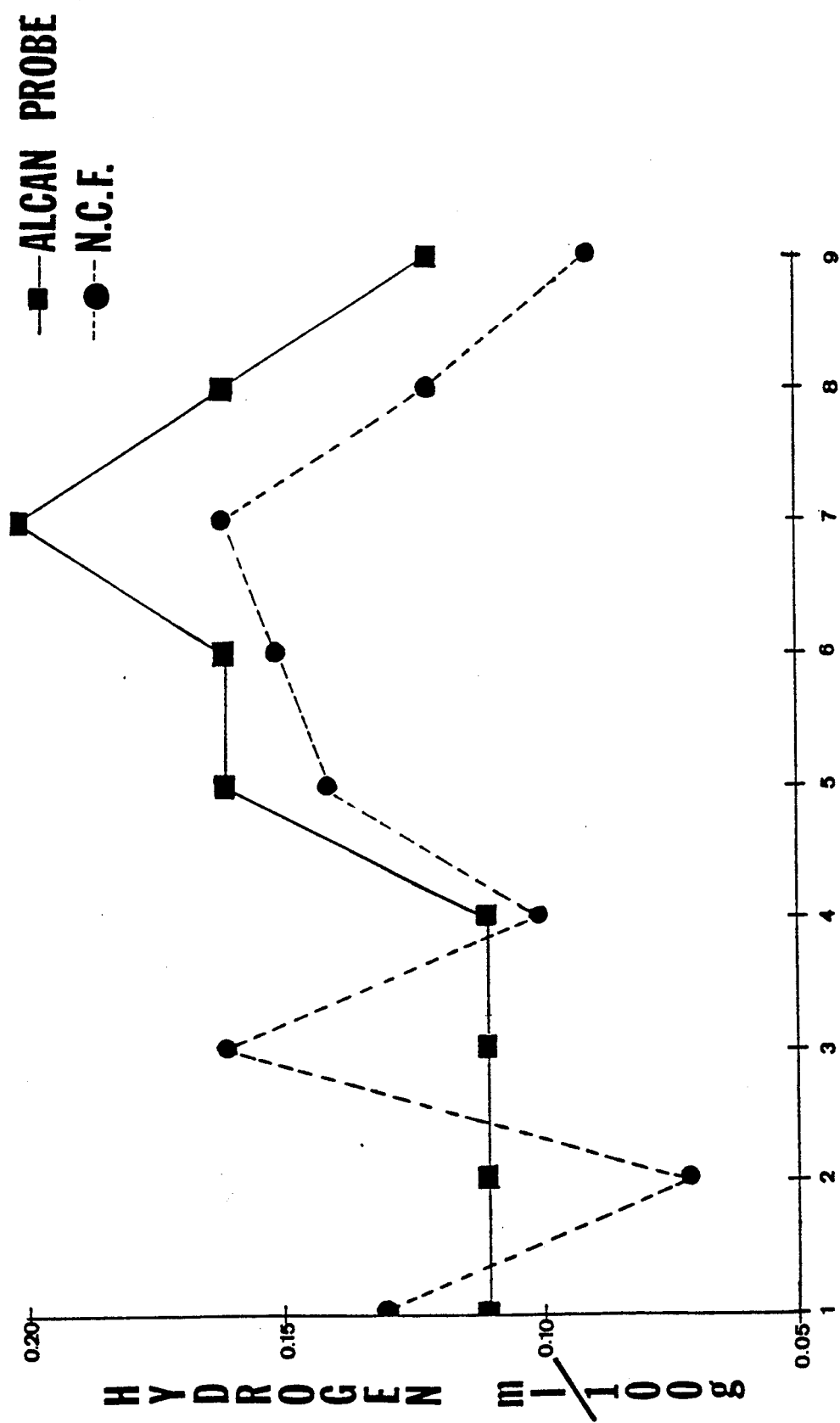

Some of the results obtained using the method of the invention are shown in FIG. 20 by a solid line, with a comparison being shown by a broken line of measurements carried out by nitrogen carrier fusion, which although a satisfactory test method is not considered to be as accurate as subfusion with Ransley samples. A description of the nitrogen carrier fusion method is given in an article by F. Degreve in J. Inst. Met., No. 47, March 1975, pages 21–26. The average difference between these two measurements is 0.03 mL/100 g.

We claim:

1. A method for the determination of gas concentration in a molten metal including the steps of:
   immersing in the molten metal an immersion probe comprising:
   a probe consisting of a gas-permeable, liquid-metal-impervious material of pore size of from 0.5 micrometers to 2,000 micrometers and of sufficient heat resistance to withstand immersion in the molten metal;
   the body having a gas inlet to its interior and a gas outlet therefrom;
   the gas inlet and outlet being spaced from one another so that gas passing from the inlet to the outlet traverses a substantial portion of the probe body interior for entrainment of gas diffusing to the interior of the body from the ambient molten metal;
   recirculating a carrier gas in a closed circuit between the probe body interior and a gas concentration determining means adapted to determine the proportion of the gas present in a mixture thereof with the carrier gas so as to entrain gas to be determined that has diffused into the probe body interior from the molten metal and continuing the recirculation for a minimum period of time sufficient to establish equilibrium between the concentration of gas to be determined in the metal and in the carrier gas; and
   after the said minimum period measuring with the gas concentrating determining means the concentration in the carrier gas of the gas to be determined.

2. A method as claimed in claim 1, wherein the gas to be determined is hydrogen and the metal is selected from aluminum, aluminum alloys and aluminum matrix composites.

3. A method as claimed in claim 1, wherein the probe body is a monolithic block of material.

4. A method as claimed in claim 1, wherein the probe body is an integral block of material.

5. A method as claimed in claim 1, and including the step of introducing a carrier gas into the closed circuit and flushing the closed circuit with the carrier gas to remove the said gas mixture therefrom.

6. A method as claimed in claim 1, wherein the probe body has a porosity of from about 5% to about 80%.

7. A method as claimed in claim 6, wherein the probe body has a porosity of from about 20% to about 60%.

8. A method as claimed in claim 7, wherein the probe body has a porosity of from 35% to 40%.

9. A method as claimed in claim 1, wherein the probe body has a permeability of from about 2 to about 2,000 Darcies.

10. A method as claimed in claim 9, wherein the probe body has a permeability of from about 10 to about 100 Darcies.

11. A method as claimed in claim 1, wherein the probe body has a pore size of from 10 micrometers to 1,000 micrometers.

12. A method as claimed in claim 11, wherein the probe body has a pore size of from 100 micrometers to 250 micrometers.

13. A method as claimed in claim 1, wherein the probe body has a volume of from about 1 cc to about 10 cc.

14. A method as claimed in claim 1, wherein the probe body is smaller in one dimension than in the other two dimensions to provide a correspondingly shorter gas diffusion path.

15. A method as claimed in claim 14, wherein the thickness of the probe body in the said smaller dimension is from about 0.5 cm to about 1.5 cm.

16. A method as claimed in claim 1, and including the step of moving the probe body and the metal relative to one another.

17. A method as claimed in claim 16, wherein the probe body and the metal are moved relative to one another by vibrating or rocking the probe in the metal.

18. A method as claimed in claim 1, and including the step of stirring the molten metal adjacent the probe body exterior to facilitate diffusion of gas from the metal into the probe.

19. A method as claimed in claim 1, wherein the exterior surface of the probe body is coated with a thin coating of a metal to facilitate its wetting by the molten metal.

20. A method as claimed in claim 19, wherein the metal is of thickness from about 10 micrometers (0.0004 in.) to 1000 micrometers (0.04 in.).

21. A method as claimed in claim 1, wherein the exterior surface of the probe body is coated with a thin coating of a material catalysing the conversion of monatomic hydrogen in the molten metal to diatomic hydrogen in the probe interior.

22. A method as claimed in claim 21, wherein the coating is of thickness from about 0.1 micrometer (0.000004 in.) to 1000 micrometers (0.04 in.).

23. A method as claimed in claim 22, wherein the material is a metal selected from platinum, palladium, rhodium and nickel.

* * * * *